United States Patent [19]

Chapleo et al.

[11] 4,397,860
[45] Aug. 9, 1983

[54] BENZODIOXANYL IMIDAZOLINE COMPOUNDS, COMPOSITIONS AND USE

[75] Inventors: Christopher B. Chapleo, Swanland; Peter L. Myers, Princes Risborough, both of England

[73] Assignee: Reckitt & Colman Products Limited, London, England

[21] Appl. No.: 340,461

[22] Filed: Jan. 18, 1982

[30] Foreign Application Priority Data

Jan. 30, 1981 [GB] United Kingdom ............... 8102906
Jul. 28, 1981 [GB] United Kingdom ............... 8123277

[51] Int. Cl.³ .................. A61K 31/415; C07D 405/04
[52] U.S. Cl. .............................. 424/273 R; 548/348
[58] Field of Search ................... 548/348; 424/273 R

[56] References Cited

U.S. PATENT DOCUMENTS 2,979,511  4/1961  Krapcho et al. .................. 544/333

OTHER PUBLICATIONS

Dabiré et al., Arch. Int. Pharmacodyn, vol. 254 (1981), pp. 252-254, 266, 267.

Primary Examiner—Robert W. Ramsuer
Attorney, Agent, or Firm—Bacon & Thomas

[57] ABSTRACT

Imidazoline derivatives of the formula

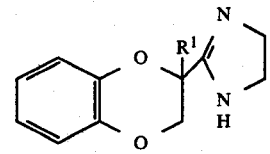

wherein $R^1$ is alkyl $C_{1-7}$, alkenyl $C_{2-4}$, cycloalkenyl $C_{4-7}$, cycloalkyl $C_{4-7}$ or phenyl; and their non-toxic salts.

Processes for the preparation and pharmaceutical compositions thereof. The compounds exhibit presynaptic $\alpha_2$-adrenoreceptor antagonism.

13 Claims, No Drawings

BENZODIOXANYL IMIDAZOLINE COMPOUNDS, COMPOSITIONS AND USE

This invention relates to imidazoline derivatives, their non-toxic salts, processes for their preparation and pharmaceutical compositions of the derivatives or their salts.

In our U.K. patent application G.B. No. 2,068,376A (published Aug. 12, 1981) and in our corresponding copending U.S. patent application Ser. No. 230,195 filed Feb. 2, 1981 we describe and claim 2-[2-(1,4-benzodioxanyl)]-2-imidazoline of formula A

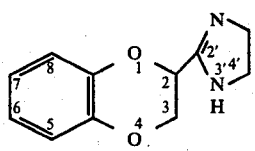

characterised in that the nuclear magnetic resonance spectrum of the compound in a protonated form exhibits multiplets in the region of $\tau 4.4$ and $\tau 5.4$, said compound being substantially free of 2-methyl-2-[2-(1,3-benzodioxolyl)]-2-imidazoline. The compound of formula A having a high degree of selectivity in blocking presynaptic $\alpha_2$-adrenoreceptors.

We have now investigated the effect of introducing a single methyl group into the molecule and have most surprisingly found that with a single exception (the 2-position) the result is very adverse with there being a profound loss of potency and selectivity.

According to this invention there are provided compounds of the formula

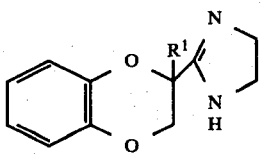

wherein $R^1$ is alkyl $C_{1-7}$, alkenyl $C_{2-4}$, cycloalkenyl $C_{4-7}$, cycloalkyl $C_{4-7}$ or phenyl; and their non-toxic salts.

Suitable values of R include methyl, ethyl, n-propyl, i-propyl, n-butyl, n-pentyl, n-hexyl, i-propenyl, cyclobut-1-enyl, cyclopent-1-enyl, cyclohex-1-enyl, cyclobutyl, cyclopentyl, cyclohexyl and phenyl.

In an aspect of the invention there are provided compounds of formula I wherein R is n-alkyl $C_{1-4}$ or alkenyl $C_{3-4}$; and their non-toxic salts.

It will be appreciated that the compounds of formula I contain an asymmetric carbon atom and it is to be understood that the invention includes both the racemic mixtures and the optically active enantiomers.

The invention also includes pharmaceutical compositions comprising a compound of Formula I or a non-toxic salt thereof, together with a pharmaceutically acceptable diluent or carrier.

Examples of non-toxic salts are those with inorganic acids such as hydrochloric acid, sulphuric or phosphoric acid; or organic acids such as acetic, propionic, malonic, succinic, fumaric, tartaric, citric or cinnamic acid. A preferred salt is the hydrochloride.

The adrenoreceptors of the sympathetic nervous system have for many years been classified into two main types namely alpha ($\alpha$) and beta ($\beta$). In recent years this classification has needed to be modified since subgroups of each type have been identified making the full classification $\alpha_1$, $\alpha_2$ and $\beta_1$, $\beta_2$. Both $\beta_1$ and $\beta_2$ as well as $\alpha_1$-adrenoreceptors are situated primarily on the surface of smooth muscle cells (postsynaptic). In contrast $\alpha_2$-adrenoreceptors have been shown by many workers (Langer, S.Z., Br. J. Pharmac., 1977, 60, 481) to be situated predominantly on the nerve terminals (presynaptic) of noradrenergic nerves. These receptors when stimulated under physiological conditions by the natural transmitter, noradrenaline, inhibit its exocytotic release. Thus, presynaptic adrenoreceptors initiate a negative feed-back loop which regulates transmitter concentration within the synaptic gap.

Agents exist which selectively stimulate (agonists) or block (antagonists) adrenoreceptors of the $\alpha_1$, $\beta_1$ and $\beta_2$ type and some of these have found clinical utility. The present invention relates to compounds with a high degree of selectivity in blocking presynaptic $\alpha_2$-adrenoreceptors.

Selective antagonism of $\alpha_2$-adrenoreceptors would inhibit the negative feedback loop which becomes operational on the release of noradrenaline from the sympathetic nerve endings. Such an inhibition would result in an increase in the synaptic concentration of noradrenaline with a consequent augmentation of the activity of the sympathetic nervous system. Such a drug would be predicted to be of value in conditions which have been postulated to be associated with a deficiency of available noradrenaline at postsynaptic adrenoreceptor sites in the central and/or peripheral nervous system. These conditions include endogenous depression, cardiac failure and conditions associated with excessive bronchoconstriction such as asthma and hay fever. Presynaptic $\alpha_2$-adrenoreceptors have also been implicated in humoral processes. For example it has been demonstrated that $\alpha_2$-adrenoreceptor agonists initiate, and antagonists inhibit, human platelet aggregation (Grant, J. A., and Scrutton, M. C., Nature, 1979, 277, 659). Thus, selective presynaptic $\alpha_2$-adrenoreceptor antagonists may be clinically desirable in pathogenic conditions in which platelet aggregation is implicated, for example, migraine.

It has been suggested recently that glucose and lipid metabolism can be controlled either directly or indirectly (via insulin) by an inhibitory mechanism involving $\alpha_2$-adrenoreceptors (Berthelsen & Pettinger, Life Sciences, 1977, 21, 595). $\alpha_2$-Adrenoreceptor antagonists may have a role to play therefore in the control of metabolic disorders such as diabetes and obesity.

Finally, the proximal tubules of the guinea-pig kidney are rich in $\alpha_2$-adrenoreceptors, the activation of which leads to sodium retention (Young & Kuhar, Eur. J. Pharmac., 1980, 67, 493) this suggests that $\alpha_2$-adrenoreceptor antagonists may produce diuresis and hence the compounds may have utility as diuretics.

The compounds of formula I in which $R^1$ is n-alkyl $C_{1-7}$, alkenyl $C_{2-4}$, cycloalkenyl $C_{4-7}$ or phenyl may be prepared from the analogous compounds of formula II

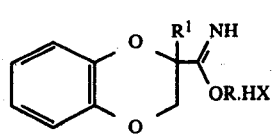

where R is alkyl $C_{1-4}$ and HX is an acid (preferably a pharmaceutically acceptable acid) by treatment with at least one molar equivalent of ethylenediamine. Preferably the reaction is carried out in a polar solvent such as methanol or ethanol. Preferably R is methyl or ethyl, HX is hydrogen chloride and the reaction is carried out in methanol or ethanol respectively.

The compounds of formula II may be prepared from the analogous cyano compounds of formula III

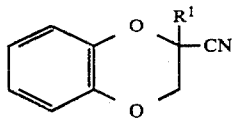
(III)

by treatment with an alcohol of formula ROH, wherein R is as hereinbefore defined, in the presence of an acid HX where HX is as hereinbefore defined. Most conveniently the alcohol is methanol or ethanol and HX is hydrogen chloride, the reaction being carried out in anhydrous diethyl ether as solvent.

A particularly convenient method of carrying out the process is to generate the compound of formula II in situ from the cyano compound of formula III. Thus for example a cyano compound of formula III dissolved in an alcohol of formula ROH (e.g. methanol or ethanol) is treated with a sodium alkoxide RONa (e.g. sodium methoxide or ethoxide), followed by reaction with hydrogen chloride (conveniently dissolved in an alcohol ROH e.g. methanol or ethanol) and at least one molar equivalent of ethylenediamine.

The compounds of formula I wherein $R^1$ is alkyl $C_{2-4}$ or cycloalkyl $C_{4-7}$ may be prepared from the analogous compounds of formula I in which $R^1$ is alkenyl $C_{2-4}$ or cycloalkenyl $C_{4-7}$ by catalytic hydrogenation in the presence of a catalyst such as palladium on carbon.

The cyano compounds of formula III where $R^1$ is n-alkyl or phenyl may be prepared from the analogous amido compounds:

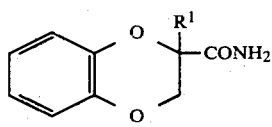
(IV)

by dehydration with for example phosphorus pentoxide or phosphorus oxychloride.

The amido compounds of formula IV may be prepared by treating the analogous acid chlorides with excess ammonia. The acid chlorides in turn have been prepared from the analogous acids of formula V by treatment with a halogenating agent such as thionyl chloride in a solvent such as toluene.

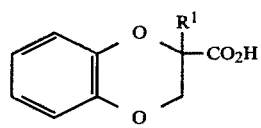
(V)

The compounds of formula V may be prepared from the analogous alcohols of formula VI by oxidation with a reagent such as potassium permanganate.

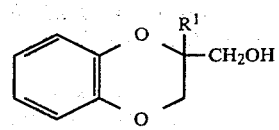
(VI)

The alcohols of formula VI may be prepared from catechol by reaction with the appropriately substituted epichlorohydrin.

The compounds of formula III wherein $R^1$ is alkenyl $C_{2-4}$ or cycloalkenyl $C_{4-7}$ may be prepared from the corresponding carbinols of formula VII or VIII

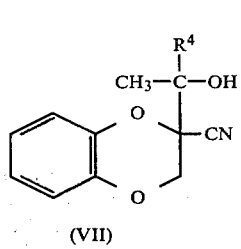
(VII)

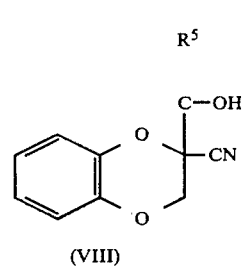
(VIII)

wherein $R^4$ is methyl or ethyl and $R^5$ is $C_{3-6}$ by dehydration using a reagent such as phosphorus pentoxide or phosphorus oxychloride.

The compounds of formula VII and VIII may be prepared from the nitrile of formula IX

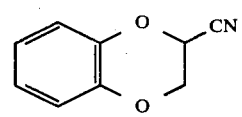
(IX)

by treatment with a carbonyl compound in the presence of a base. Examples of carbonyl compounds include acetone and cyclopentanone and of bases potassium carbonate.

The invention is illustrated by the following Examples in which temperatures are in degrees Celsius.

The various compounds and intermediates were examined by thin layer chromatography (t.l.c.) on silica gel plates (Merck, Kieselgel 60 $F_{254}$). Melting points were determined on a Kofler hot stage apparatus of a Buchi apparatus in glass capillary tubes and are uncorrected. I. R. spectra were recorded on a Perkin-Elmer 710 B spectrophotometer.

EXAMPLE 1

2-[2-(2-Methyl-1,4-benzodioxanyl)]-2-imidazoline hydrochloride (a) 2-Methyl-1,4-benzodioxan-2-carboxylic acid A mixture (23.7 g) of 2-hydroxymethyl-2-methyl-1,4-benzodioxan and 3-hydroxy-3-methyl-2H-1,5-benzodioxepine (~3:1 ratio; prepared according to the method of A. Salimbeni, E. Manghisi, J. Heterocyclic Chem., 17, 489, 1980) was stirred with 1 N aqueous sodium hydroxide solution (135 ml) and cooled to 0°-10°. A solution of potassium permanganate (42 g) in water (165 ml) was added slowly so that the temperature was maintained below 10°. After 48 hours at room temperature the mixture was filtered and the filtrate acidified with 1 M aqueous sulphuric acid and extracted with methylene chloride. The extracts were washed with aqueous sodium bicarbonate solution and the aqueous layer was acidified with sulphuric acid. Extraction with methylene chloride followed by washing, drying and evaporation of the extracts gave the carboxylic acid (11.5 g); m.p. 125°–129.5°.

(b) 2-Methyl-1,4-benzodioxan-2-carboxamide

A mixture of 2-methyl-1,4-benzodioxan-2-carboxylic acid (10.28 g) and thionyl chloride (7.8 ml) in anhydrous toluene (40 ml) was heated for 1 hour at 90°–100°. Removal of solvent and excess thionyl chloride in vacuo gave the crude carbonyl chloride which slowly solidified. A solution of this intermediate in anhydrous dioxan (25 ml) was added slowly to stirred aqueous ammonia (d 0.88; 26 ml) with cooling (0°–10°). After 1 hour water (300 ml) was added and the solid was collected by filtration, washed with water and then dried to yield the carboxamide (8.3 g); m.p. 127°–128.5°.

(c) 2-Cyano-2-methyl-1,4-benzodioxan

A stirred mixture of 2-methyl-1,4-benzodioxan-2-carboxamide (8.17 g), phosphorus pentoxide (17 g) and anhydrous toluene (175 ml) was heated under reflux for 4 hours. On cooling the supernatant was decanted from the residue, the latter being washed by decantation with more toluene. Filtration and evaporation of the solvent gave a solid residue (5.18 g). Crystallisation from ethanol yielded the cyano compound (4.4 g); m.p. 88°–89°.

(d) 2-[2-(2-Methyl-1,4-benzodioxanyl)]-2-imidazoline hydrochloride

A mixture of 2-cyano-2-methyl-1,4-benzodioxan (0.61 g), sodium methoxide (16 mg) and methanol (2.3 ml) was stirred for 18 hours to give an almost clear solution. On cooling to 0°–10° a solution of ethylenediamine (0.235 g) in methanol (1 ml) was added dropwise with stirring. After a few minutes a solution of hydrogen chloride in methanol (0.65 ml of 5.6 M solution) was added dropwise and the mixture was then allowed to warm to room temperature. After 16 hours the mixture was made slightly acid with methanolic hydrogen chloride and filtered to remove the solid. Addition of diethyl ether to the filtrate gave a solid which was collected by filtration (0.84 g; 2 crops). Recrystallisation from ethanol-diethyl ether containing hydrogen chloride gave after drying the imidazoline hydrochloride; m.p. 258°–261° (analysed as ¼ hydrate).

EXAMPLE 2

2-[2-(2-Ethyl-1,4-benzodioxanyl)]-2-imidazoline

(a) 2-Hydroxymethyl-2-ethyl-1,4-benzodioxan

A stirred mixture of catechol (14.0 g), 2-ethyl-epichlorohydrin (15.3 g), sodium hydroxide (5.1 g) and water (50 ml) was heated at 90° under an atmosphere of nitrogen for 4 hours. On cooling water was added and the product was extracted with methylene chloride. The combined extracts were washed with 2 N aqueous sodium hydroxide solution, water and brine, dried and evaporated to leave an oil (10.8 g); IR $\nu_{max}$ 3650–3200, 3000–2850 cm$^{-1}$.

(b) 2-[2-(2-Ethyl-1,4-benzodioxanyl)]-2-imidazoline

The above 2-ethyl-benzodioxan methanol was converted to the corresponding imidazoline compound by the methods a–d of Example 1. In method (d) after the addition of the methanolic hydrogen chloride solution most of the solvent was removed in vacuo and the residue was partitioned between aqueous sodium bicarbonate solution and ethyl acetate. Drying of the organic phase followed by evaporation of the solvent gave a solid which was triturated with light petroleum (60°–80°) to yield the imidazoline free base; m.p. 98°–100°.

EXAMPLE 3

2-[2-(2-Phenyl-1,4-benzodioxanyl)]-2-imidazoline

Catechol and 2-phenyl epichlorohydrin were reacted to give the intermediate 2-hydroxymethyl-2-phenyl-1,4-benzodioxan (method (a) of Example 2) which was converted to the imidazoline compound by method (b) of Example 2. The free base was recrystallised from light petroleum (60°–80°); m.p. 114.5°–116°.

EXAMPLE 4

2-[2-(2-Isopropenyl-1,4-benzodioxanyl)]-2-imidazoline

(a) 2-Cyano-2-(1-hydroxy-1-methylethyl)-1,4-benzodioxan

A suspension of 2-cyano-1,4-benzodioxan (40 g) and anhydrous potassium carbonate (176 g) in acetone (500 ml) was stirred and heated under reflux for 5 days. The mixture was cooled and inorganic salts removed by filtration. After evaporation of the acetone in vacuo the residue was partitioned between methylene chloride and 2 N aqueous sodium hydroxide solution. The organic layer was washed with 2 N aqueous sodium hydroxide solution (x2), 5% hydrochloric acid, brine and then dried by passage through absorbent cotton wool. Evaporation in vacuo gave an orange oil (37 g). The required product was isolated by passage through a silica column (300 g) with methylene chloride as eluent. Those fractions, which when examined by t.l.c. had $R_f$ 0.2 (CHCl$_3$) were combined and evaporated in vacuo to give the desired hydroxy compound (14.5 g); m.p. 63°–65° (18 g of unreacted 2-cyano-1,4-benzodioxan were recovered from the column).

(b) 2-Cyano-2-isopropenyl-1,4-benzodioxan

A solution of the above hydroxy compound (0.80 g) in dry pyridine (8 ml) at room temperature was treated dropwise with phosphorus oxychloride (1 ml) over 5 minutes. The solution was then heated at 60°–70° for 18 hours, cooled and poured carefully onto ice-water. The mixture was extracted with methylene chloride (3×50 ml), the extracts washed with brine, dried and evaporated to give the desired isopropenyl compound (0.62 g); $R_f$ 0.75 (CHCl$_3$).

(c) 2-[2-(2-Isopropenyl-1,4-benzodioxanyl)]-2-imidazoline

The above isopropenyl compound was reacted with ethylenediamine as described in method (d) of Example 1. After the addition of the methanolic hydrogen chloride solution most of the solvent was removed in vacuo and the residue was partitioned between aqueous sodium bicarbonate solution and methylene chloride. Drying of the organic phase followed by evaporation of the solvent gave a solid which was recrystallised from light petroleum (60°–80°) to yield the imidazoline free base; m.p. 108°–110°.

EXAMPLE 5

2-[2-(2-Isopropyl-1,4-benzodioxanyl)]-2-imidazoline

A solution of 2-[2-(2-isopropenyl-1,4-benzodioxanyl)]-2-imidazoline (0.80 g) in ethanol (8 ml) with 10% palladium on carbon (80 mg) was hydrogenated at atmospheric pressure and room temperature for 6.5 hours. The mixture was filtered, the palladium residues washed with ethanol (2×10 ml) and the combined filtrates evaporated to dryness at reduced pressure. The resultant solid (0.8 g) was recrystallised from light petroleum (60°–80°) to give the isopropyl benzodioxan (0.3 g); m.p. 124°–125°.

EXAMPLE 6

2-[2-(2-Cyclohex-1'-enyl-1,4-benzodioxanyl)]-2-imidazoline

This was prepared by the methods of a–c of Example 4 using cyclohexanone in place of acetone with reaction at ~90°. The product had m.p. 122°–124°.

EXAMPLE 7

2-[2-(2-Cyclopent-1'-enyl-1,4-benzodioxanyl)]-2-imidazoline

This was prepared by the methods a–c of Example 4 using cyclopentanone in place of acetone with reaction at ~90°. The product had m.p. 83°–85°.

EXAMPLE 8

2-[2-(2-n-Propyl-1,4-benzodioxanyl)]-2-imidazoline

This was prepared by the method of Example 2 using 2-n-propylepichlorohydrin (prepared by base treatment of 1-chloro-2-hydroxy-2-chloromethylpentane obtained by reaction of n-propylmagnesium bromide with 1,3-dichloroacetone in anhydrous toluene). and had m.p. 113°–115°.

EXAMPLE 9

2-[2-(2-Cyclobut-1'-enyl-1,4-benzodioxanyl)]-2-imidazoline hydrochloride

This was prepared by the methods a–c of Example 4 using cyclobutanone with tetrahydrofuran as co-solvent in place of acetone with reaction at ~65° C. The product had $R_f$ 0.38 (CHCl$_3$/methanol 4:1 v/v).

EXAMPLE 10

2-[2-(2-Cyclopentyl-1,4-benzodioxanyl)]-2-imidazoline

A solution of 2-[2-(2-cyclopent-1'-enyl-1,4-benzodioxanyl)]-2-imidazoline (0.50 g) in ethanol (10 ml) with 10% palladium on carbon (80 mg) was hydrogenated at atmospheric pressure and room temperature for 3.5 hours. The mixture was filtered and the filtrate evaporated to dryness at reduced pressure to give a brown oil (0.5 g). The oil was partitioned between 2N aqueous hydrochloric acid and diethyl ether. The aqueous layer was basified with sodium bicarbonate and then extracted with diethyl ether. The dried organic phase was evaporated at reduced pressure to leave a solid (0.5 g) which was recrystallised from hexane to give a white solid (0.10 g); m.p. 135°–136°.

The pharmacological activity of the compounds of the invention have been determined according to the following procedures.

1. Pre- and postsynaptic α-adrenoreceptor antagonism in isolated tissue experiments Presynaptic $\alpha_2$-adrenoreceptor antagonism was assessed by determining pA$_2$ values against the inhibitory effects of clonidine, a well known presynaptic $\alpha_2$-adrenoreceptor agonist, on the rat vas deferens stimulated at a frequency of 0.1 Hz according to the method of Doxey, J. C., Smith, C.F.C., and Walker, J. M., Br. J. Pharmac., 1977, 60, 91.

This is vitro model is particularly useful as an initial screen for studying presynaptic activity in isolation since the physiological nature of the vas deferens tissue is such that the postsynaptic receptors located therein are particularly inaccessible to exogenous agents. In consequence an alternative tissue, the rat anococcygeus muscle is used to establish postsynaptic $\alpha_1$-adrenoreceptor activity. Antagonism of noradrenaline contractions is used to determine pA$_2$ values at postsynaptic $\alpha_1$-adrenoreceptors. The ratio of presynaptic $\alpha_2$-adrenoreceptor antagonism (versus clonidine on the rat vas deferens) to postsynaptic $\alpha_1$-adrenoreceptor antagonism (versus noradrenaline contractions on the rat anococcygeus muscle) is used to assess adrenoreceptor selectivity. The pA$_2$ value for the compound of Example 1 is shown in Table 1. Table 1 also includes the results for four standard drugs: (i) the non-selective α-adrenoreceptor antagonist, phentolamine, (ii) the selective presynaptic antagonist, yohimbine, (iii) the highly selective postsynaptic antagonist, prazosin and (iv) the antidepressant, mianserin which shows non-selective pre- and postsynaptic adrenoreceptor antagonist properties as part of its pharmacological profile.

TABLE 1

| Compound | Presynaptic antagonism pA$_2$ vs Clonidine (vas deferens) | Postsynaptic antagonism pA$_2$ vs Noradrenaline (anococcygeus) | Pre/post synaptic ratio |
|---|---|---|---|
| Example 1 | 8.6 | 5.6 | 871 |
| Phentolamine | 8.4 | 7.7 | 4.8 |
| Yohimbine | 8.2 | 6.4 | 60 |
| Prazosin | 5.9 | 8.2 | 0.005 |
| Mianserin | 7.3 | 6.6 | 5.0 |

The results are the mean of a minimum of 5 experiments.

It can be seen in Table 1 that of the compounds studied, the compound of Example 1 was the most potent presynaptic $\alpha_2$-adrenoreceptor antagonist and was moreover the most selective for presynaptic sites.

2. Presynaptic $\alpha_2$-adrenoreceptor antagonism in the pithed rat (1) Rat vas deferens-intravenous activity.

This test model extends the evaluation of presynaptic $\alpha_2$-adrenoreceptor antagonism versus clonidine on the rat vas deferens to the in vivo situation. Blood pressure and stimulation induced contractions of the vas deferens were monitored in pithed rats using the method of Brown, J., Doxey, J. C., Handley, S. and Virdee, N., Recent Advances in the Pharmacology of Adrenoceptors, Elsevier North Holland, 1978. Clonidine (100 μg/kg, i.v.) causes a prolonged pressor response and a prolonged inhibition of vas deferens contractions. The test drugs were injected intravenously in a cumulative dosing schedule and their abilities to reverse the inhibition of hypogastric nerve stimulation reflected their presynaptic antagonism. Table 2 shows the doses of antagonists which caused a 50% reversal of the inhibition of hypogastric nerve stimulation.

TABLE 2
Relative antagonist potencies at presynaptic $\alpha_2$-adreno-receptors in the pithed rat

| Compound | i.v. dose of antagonist causing 50% reversal of clonidine block on vas deferens mg/kg |
|---|---|
| Example 1 | 0.04 |
| Yohimbine HCl | 0.86 |
| Mianserin HCl | >4.4 |
| Phentolamine mesylate | 0.12 |

The results are the mean of a minimum of 4 rats.

Under the chosen experimental conditions all of the compounds studied, with the exception of mianserin produced a complete reversal of the inhibitory effects of clonidine on hypogastric nerve stimulation. The maximum reversal seen with mianserin was 36% at a cumulative intravenous dose of 4.4 mg/kg. It can be seen from Table 2 that the compound of Example 1 is clearly the most potent presynaptic $\alpha_2$-adrenoreceptor antagonist of those studied.

The pharmacological activity of the compound of Example 1 (in formula I $R^1$=methyl) has been compared with the activities of the isomeric compounds in which the methyl group is situated at differing positions in formula A. The procedures involved the measurement of agonist or antagonist activity at pre- and post-synaptic $\alpha$-adrenoreceptors.

In the procedures outlined below agonist potency of the compounds was determined with respect to standard agents whereas antagonist potency was related to that of the compound of formula A. Pre- and post-synaptic studies were carried out in the mouse vas deferens and rat anococcygeus muscle respectively.

Pre-synaptic studies ($\alpha_2$)

The mouse vas deferens was stimulated at low frequency (0.1 Hz) and the "twitch" responses recorded. Pre-synaptic $\alpha_2$-adrenoreceptor agonist activity was determined by assessing the ability of compounds to inhibit these contractions. When inhibition was seen the potency of the individual compounds was related to that of the standard $\alpha_2$-adrenoreceptor agonist clonidine.

In the antagonist studies the same experimental conditions were used except that the twitch response was suppressed by including clonidine (30 ng/ml) in the physiological solution. The abilities of compounds to reverse the inhibitory effects of clonidine were determined and their potencies related to that of the compound of formula A.

Post-synaptic studies ($\alpha_1$)

The rat anococcygeus muscle was used for both agonist and antagonist studies. The ability of compounds to induce contractions of the anococcygeus muscle reflected post-synaptic $\alpha_1$-adrenoreceptor agonist activity. The potencies of the compounds with contractile properties were determined with respect to phenylephine which is a selective post-synaptic $\alpha_1$-adrenoreceptor agonist.

Antagonist activity was examined by determining the inhibitory effects of the compounds on noradrenaline-induced contractions of the anococcygeus muscle. The concentration of compound which produced a dose-ratio of 2 against noradrenaline was determined and related to the potency of the compound of formula A.

The results are set out in Table 3, the first column indicating the position of the methyl substituent on Formula A. From the Table it can be seen that the compound of Example 1 is rather more than twice as selective as the compound of formula A. None of the other 7 compounds are as selective as the compound of formula A, and as $\alpha_2$-antagonists are of considerably reduced potency. In some cases $\alpha_2$-agonism becomes a feature of their profile.

TABLE 3

| Compound | $\alpha_2$ potency Agonism[1] | $\alpha_2$ potency Antagonism[2] | $\alpha_1$ potency Agonism[3] | $\alpha_1$ potency Antagonism[4] | $\alpha_2/\alpha_1$[5] |
|---|---|---|---|---|---|
| Ex. 1 | I.A. | 0.67 | I.A. | 0.28 | 2.4 |
| 3-methyl | I.A. | 0.004 | I.A. | <0.023 | — |
| 5-methyl | 0.1 | 0.13 | 1.0 | Potentiation 20ng/ml | — |
| 6-methyl | I.A. | 0.08 | I.A. | <0.11 | 0.7 |
| 7-methyl | I.A. | 0.08 | 0.004 | 0.125 | 0.64 |
| 8-methyl | 0.01 | 0.5 | 2.1 | — | — |
| $2^1$-methyl | I.A. | 0.0003 | I.A. | 0.1 | 0.003 |
| $3^1$-methyl | I.A. | 0.003 | I.A. | 1.0 | 0.003 |

[1]Potency relative to clonidine = 1
[2] and [4]Potency relative to the compound of formula A
[3]Potency relative to phenylephrine = 1
[5]Selectivity relative to the compound of formula A
I.A. = inactive.

The invention also includes the use of a compound of Formula I or a non-toxic salt thereof in the treatment of depression and a method of treating depression which comprises administering to humans an antidepressant effective amount of a compound of Formula I or a non-toxic salt thereof.

The pharmaceutical compositions may be in a form suitable for oral, rectal or parenteral administration. Such oral compositions may be in the form of capsules, tablets, granules or liquid preparations such as elixirs, syrups or suspensions.

Tablets contain a compound of Formula I or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or Kaolin in a hard gelatine capsule.

Compositions for parenteral administration may be in the form of sterile injectable preparations such as solutions or suspensions in for example water, saline or 1,3-butane diol.

For the purposes of convenience and accuracy of dosing the compositions are advantageously employed in a unit dosage form. For oral administration the unit dosage form contains from 1 to 200 mg, preferable 10 to 50 mg of the compound of Formula I or a non-toxic salt thereof. Parenteral unit dosage forms contain from 0.1 to 10 mg of the compound of Formula I or a non-toxic salt thereof per 1 ml of the preparation.

The invention is further illustrated by the following Examples of compositions in which all parts are by weight.

EXAMPLE 1

A mixture of one part 2-[2-(2-methyl-1,4-benzodioxanyl)]-2-imidazoline hydrochloride and four parts microcrystalline cellulose together with 1% of magnesium stearate is compressed into tablets. Conveniently the tablets are of such a size as to contain 10, 25 of 50 mg of the active ingredient.

EXAMPLE II

A mixture of one part 2-[2-(2-methyl-1,4-benzodioxanyl)]-2-imidazoline hydrochloride and four parts spray dried lactose together with 1% magnesium steatate is filled into hard gelatine capsules. The capsules may conveniently contain 10, 25 or 50 mg of the active ingredient.

We claim:
1. A compound of formula:

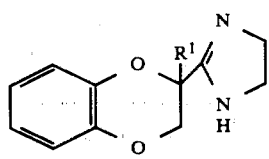

(I)

wherein $R^1$ is alkyl $C_{1-7}$, alkenyl $C_{2-4}$, cycloalkenyl $C_{4-7}$; and its non-toxic salts.

2. A compound of formula I given in claim 1 wherein $R^1$ is n-alkyl $C_{1-4}$ or alkenyl $C_{3-4}$; and its non-toxic salts.

3. 2-[2-(2-Methyl-1,4-benzodioxanyl)]-2-imidazoline.

4. 2-[2-(2-Ethyl-1,4-benzodioxanyl)]-2-imidazoline.

5. 2-[2-(2-n-Propyl-1,4-benzodioxanyl)]-2-imidazoline.

6. 2-[2-(2-Isopropenyl-1,4-benzodioxanyl)]-2-imidazoline.

7. 2-[2-(2-Cyclobut-1'-enyl-1,4-benzodioxanyl)]-2-imidazoline.

8. A pharmaceutical composition for selective presynaptic $\alpha_2$-adrenoreceptor antagonist use comprising a compound as claimed in claim 1, or a non-toxic salt thereof in an amount effective for said use together with a pharmaceutically acceptable diluent or carrier.

9. A pharmaceutical composition as claimed in claim 8 which is in unit dosage form.

10. A pharmaceutical composition as claimed in claim 9 for oral administration wherein each unit dosage contains from 1 to 200 mg of the compound of formula I or a non-toxic salt thereof.

11. A pharmaceutical composition as claimed in claim 10 wherein each unit dosage contains from 10 to 50 mg of the compound of formula I or a non-toxic salt thereof.

12. A pharmaceutical composition as claimed in claim 9 for parenteral administration wherein each unit dosage contains from 0.1 to 10 mg of the compound of formula I or a non-toxic salt thereof per 1 ml of the composition.

13. A method of treating depression which comprises administering to a human an antidepressant effective amount of a compound as claimed in claim 1 or a non-toxic salt thereof.

* * * * *

UNITED STATES PATENT AND TRADEMARK OFFICE
CERTIFICATE OF CORRECTION

PATENT NO. : 4,397,860
DATED : August 9, 1983
INVENTOR(S) : CHAPLEO et al

It is certified that error appears in the above—identified patent and that said Letters Patent is hereby corrected as shown below:

Column 4, Formula VIII, correct the structural formula to read:

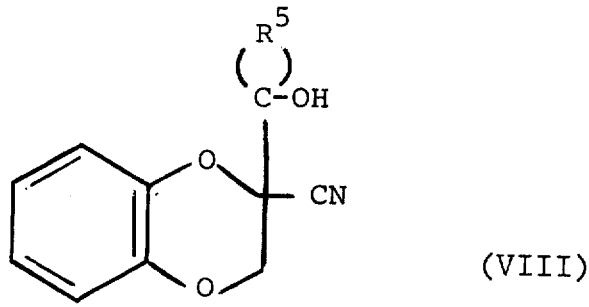

(VIII)

Signed and Sealed this

Twenty-fifth Day of October 1983

[SEAL]

Attest:

Attesting Officer

GERALD J. MOSSINGHOFF
Commissioner of Patents and Trademarks